United States Patent [19]
Fedorov et al.

[11] Patent Number: 5,135,466
[45] Date of Patent: Aug. 4, 1992

[54] METHOD FOR TREATMENT OF DISEASES OF THE OPTIC TRACT AND A DEVICE FOR CARRYING SAID METHOD INTO EFFECT

[76] Inventors: Svyatoslav N. Fedorov, pereulok Dostoevskogo, 1/21, kv. 32; Leonid F. Linnik, ulitsa Deguninskaya, 17, kv. 36; Gennady M. Antropov, ulitsa B. Akademicheskaya, 24a, kv. 117; Leonid N. Arnautov, ulitsa Kharkovskaya, 1, korpus 2, kv. 318; Vladimir V. Ippolitov, ulitsa Lavochkina, 6, korpus 2, kv. 143; Valentin F. Streltsov, Korovinskoe shosse, 25/30, kv. 78; Alexandr P. Stromakov, ulitsa Matveevskaya, 1,kv. 49; Nina A. Shigina, ulitsa Leskova, 30, kv. 5, all of Moscow, U.S.S.R.

[21] Appl. No.: 778,490

[22] Filed: Oct. 17, 1991

Related U.S. Application Data

[62] Division of Ser. No. 713,578, Jun. 11, 1990, Pat. No. 5,085,627.

[30] Foreign Application Priority Data

Aug. 18, 1988 [SU] U.S.S.R. .................. 4469065

[51] Int. Cl.$^5$ ............................................. A61N 2/12
[52] U.S. Cl. ...................................... 600/11; 600/9
[58] Field of Search ............... 600/9, 10, 11, 12, 13, 600/14, 15; 74/DIG. 4; 433/133

[56] References Cited

U.S. PATENT DOCUMENTS

| | | | |
|---|---|---|---|
| 4,084,209 | 4/1978 | Hilal | 600/11 |
| 4,486,176 | 12/1984 | Tordieu et al. | 433/133 |
| 4,727,857 | 3/1980 | Hörl | 600/14 |
| 4,732,156 | 3/1988 | Nakamura | 128/662.06 |

FOREIGN PATENT DOCUMENTS

3324119  1/1985  United Kingdom ............ 600/9

*Primary Examiner*—William E. Kamm
*Assistant Examiner*—Scott R. Akers
*Attorney, Agent, or Firm*—Burgess, Ryan and Wayne

[57] ABSTRACT

A method for treatment of diseases of the optic tract resides in applying a rotating magnetic field, which rotates at a variable angular velocity and its rotation is brought in synchronism with the blood flow pulsation in the internal carotid artery, is applied to the bridge of the nose, to the upper portion of the orbit of both eyes, to the temporal areas, to both of the auriculo-temporal regions, and to the region of a projection of the visual analyzers.

A device for treatment of diseases of the optic tract, comprising a housing, accommodating a drive and a main permanent magnet whose axle is connected to the shaft of a drive through an elastic element. Besides, a magnetic brake is accommodated in the housing in the zone of action of the magnetic field.

9 Claims, 4 Drawing Sheets

METHOD FOR TREATMENT OF DISEASES OF THE OPTIC TRACT AND A DEVICE FOR CARRYING SAID METHOD INTO EFFECT

This is a division of application Ser. No. 713,578, filed Jun. 11, 1990 now U.S. Pat. No. 5,085,627.

FIELD OF THE INVENTION

The invention relates generally to medicine and more specifically to a method for treatment of diseases of the optic tract and to a device for carrying said method into effect.

The invention is applicable for treatment of optic tract affections under clinical or outpatient conditions, as well as for treatment of proctologic and gynecologic diseases, morbid conditions secondary to injuries, parodontosis, chronic inflammatory diseases of the genitalia, and atrophy of the auditory nerve.

BACKGROUND OF THE INVENTION

Known in the present state of the art is a method for treatment of neuritis of the optic nerve (SU, A, 927,246) by virtue of an effect produced by a magnetic field having an intensity of from 200 to 400 Oe. Sources of the magnetic field are arranged at the level of a straight line passing through the external auditory pores, and the area of the optic nerve is exposed to the effect of the magnetic field for 15 minutes, a treatment course consisting of 15 to 20 such 15-minute sessions. Three or four treatment courses are carried out at a one- to three-month interval.

However, said method is not adequately efficient when used for treatment of optic tract diseases and suffers from substantial disadvantages.

The method makes use of a permanent magnetic field, which is less efficient than a variable field and the more so a pulsed one.

A permanent magnetic field involves prolonged treatment sessions and hence longer treatment courses.

The method in question supposes only one area to be acted upon, whereas the optic tract features a definite extent so that all the areas of the optic tract, that is, the retina, optic nerve, chiasm, geniculate body, and visual analyzers of the cortex of both cerebral hemispheres, cannot be exposed to the effect of a magnetic field with the same field intensity, i.e., the effect on the other areas of the optic tract is much less efficient.

Known in the art is a method for treatment of reticular dystrophy (SU, A, 1,204,211), consisting in exposure of the eye to the effect of a permanent magnetic field, the procedure involving application of a magnet having an area of 5.0 to 7.0 cm$^2$ and magnetic induction of 150 to 200 mT, with its southseeking pole to the patient's temporal region, whereupon the axis of the magnet is aligned with a horizontal straight line passing through the external angle of the infraobital margin, a treatment session taking 15 to 20 minutes.

However, the aforesaid method is not adequately effective in treatment of optic tract diseases, since it makes use of a permanent magnetic field, which is less efficient than a variable or a pulsed field.

Moreover, exposure to the effect of a permanent magnetic field involves prolonged treatment sessions and courses, while application of a curative action upon only one optic tract element fails to provide magnetic field application to other areas of the optic tract, thereby affecting the curative effect of said optic tract areas.

Further on, a prolonged period of treatment is concerned with the fact that, whenever both eyes are to be treated, the essence of the proposed method allows only one eye to be treated at a time, since simultaneous treatment of both eyes affects badly the rheo-ophthalmic indices of both eyes, a feature that adds more to the duration of the treatment period.

An applicator for magnetotherapy of the eye (SU, A, 1,139,446) is known to comprise a body and a magnetic element. The applicator is provided with a coordinate ring and a number of additional magnetic elements, said magnetic elements having polepieces and are situated in the body slots with a possibility of radial and longitudinal travel and rotation, while the body itself is turnable with respect to the coordinate ring.

However, the invention under consideration suffers from some disadvantages, namely, it is constructionally intended for frontal arrangement on the anterior eye portion and cannot be applied to other ocular portions wanting magnetic therapy, thereby being ineffective for treatment of diseases of the entire optic tract. Besides, the present device fails to provide synchronism of the magnetic field effect with the blood flow pulsation in the internal carotid artery, which affects adversely the efficacy of treatment.

One prior-art magnetotherapy device (DE, A, 1,3221544) is known to comprise a housing accomodating a permanent magnet and a drive whose shaft is associated with the axle of the permanent magnet.

The operating principle of the known device is based on the fact that a rotating magnetic field is established round a rotary permanent magnet, which magnetic field is used to produce a curative effect onto various pathologic areas. A characteristic feature of the aforesaid known device is the fact that the permanent magnet rotates uniformly and its rotation develops a sinusoidally variable space magnetic field, which prolongs the treatment period and affects the curative effect.

The device fails to provide substantially intense induced electric fields when bringing permanent magnet rotation in synchronism with blood flow pulsation in the internal carotid artery, since to establish high-intensity electric fields requires very high values of magnetic field induction (of the order of 1 T), which is practically unattainable in the device under consideration.

The disadvantages stated hereinbefore are fraught with untowards side effects, such as headache, abnormally intraocular pressure, which also affects the efficacy of treatment of the optic tract diseases.

SUMMARY OF THE INVENTION

It is an object of the invention to enhance the visual function.

It is another object of the invention to enhance the efficacy of treatment.

It is a further object of the invention to curtail the treatment time.

These objects are accomplished due to the fact that in a method for treatment of diseases of the optic tract, comprises exposing it to the effect of a magnetic field, according to the invention, the magnetic field is applied to the bridge of the nose, the upper portion of the orbit of both eyes with the eyelids closed, the temporal areas close to the external orbital margin of both eyes, to both of the auriculo-temporal regions at the level of a projection of the optic decussation, and to the region of a projection of the visual analyzers on the occipital protuberances; when applied to said regions the magnetic field is rotated at a variable angular velocity and its rotation is brought in synchronism with the blood flow pulsation in the internal carotid artery.

It is also expedient that a maximum magnetic field induction in the proposed method be from 0.1 to 0.25 T.

It is also expedient that the effect of a rotating magnetic field be applied to each of the aforesaid regions for 1 to 5 minutes.

These objects are accomplished also due to the fact that a device for treatment of diseases of the optic tract, comprising a housing which accommodates a drive and at least one main permanent magnet whose axle is connected to the drive shaft, according to the invention, is provided with a magnetic brake accommodated in the housing in the area of the magnetic field effect, while the axle of the permanent magnet is connected to the drive shaft through an elastic element.

It is also expedient that the magnetic brake of the device proposed herein be made as at least one ferromagnetic rod.

It is also favourable that the magnetic brake be made as at least one permanent magnet.

It is also expedient that the device be provided with a shield having a window and arranged round the permanent magnet, said shield being made of a high-conductance material.

Thus, practical application of the aforedescribed method for treatment of diseases of the optic tract and the device for carrying said method into effect makes it possible to enhance visual functions from two to fifteen times, depending on etiology of a disease, as for acuity of vision, to increase efficacy of treatment and to cut down the treatment period to 15 days, i.e., one treatment cycle consisting of 15 magnetotherapy sessions.

BRIEF DESCRIPTION OF THE DRAWINGS

In what follows the invention is illustrated by specific exemplary embodiments thereof with reference to the accompanying drawings, wherein.

DETAILED DESCRIPTION OF THE INVENTION

Figure 1:
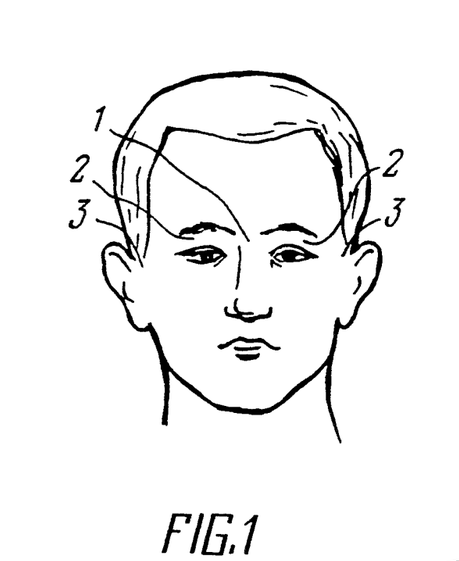
FIGS. 1 through 3 show areas on human head which are exposed to the effect of a rotating magnetic field, according to the invention.
Figure 2:
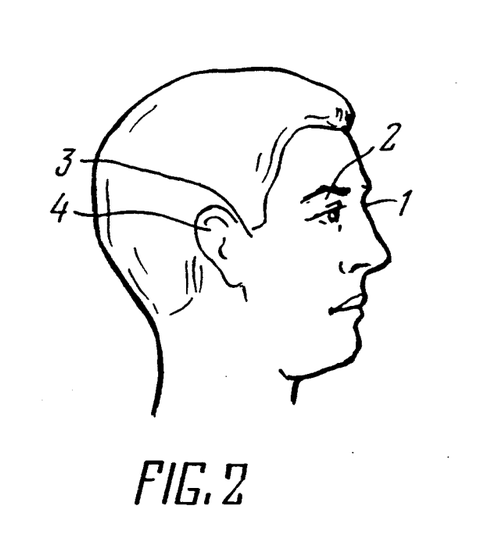
Figure 3:
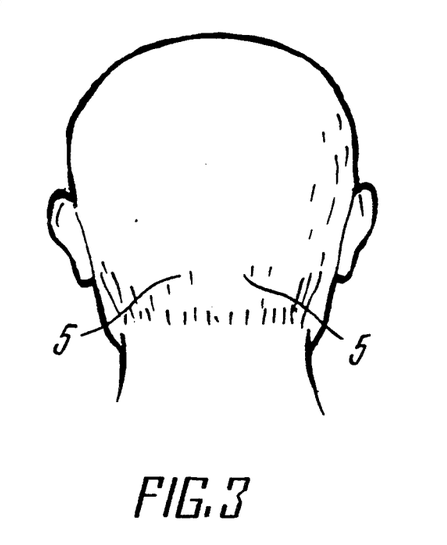

The method for treatment of diseases of the optic tract consists in that a magnetic field rotating at a variable angular velocity, is applied to a region 1 (FIGS. 1, 2) of the bridge of the nose, to an upper portion of the orbit of both eyes (with the eyelids closed), to the temporal areas close to an external orbital margin 3 of both eyes, to both auriculo-temporal areas 4 at the level of a projection of the optic decussation, and to the region of a projection of visual analyzers on occipital protuberances (FIG. 3).

Rotation of the magnetic field is brought in synchronism with the blood flow pulsation in the internal carotid artery, and a maximum magnetic field induction is within 0.1 and 0.25 T.

As it has been demonstrated by clinical practice the sequence of conduction of stimulation of said areas does not matter. Considered below is one of the variants of the sequence of stimulation of said areas.

Prior to conducting a treatment procedure the housing of the device for treatment of diseases of the optic tract is disinfected with ethyl alcohol at the spot where the permanent magnet is located. Then the rotating magnetic field is synchronized, as for the rotation frequency, with the blood flow pulsation in the internal carotid artery by selecting the rotation frequency of the main permanent magnet equal to the carotid pulsation rate, using conventional methods. Synchronization is carried out by measuring the pulse by well-known pulse measuring means such as, for example, those methods disclosed in U.S. Pat. Nos. 3,139,036 and 3,980,075, incorporated herein by reference. The signal generated by the pulse measuring means is used as a control signal for starting the drive means. Each time the systole appears, the drive means is started up and when the systole is completed, this corresponds with the end of the rotation of the drive means. Thereafter the device for treatment of diseases of the optic tract is so positioned that the main permanent magnet be placed closely first on the upper portion 2 (FIGS. 1, 2) of the orbit of one eye, then of the other eye, the eyelids being closed, while exposure time of each of said areas to the effect of the rotating magnetic field ranges from 1 to 5 minutes. Next the main permanent magnet is placed in the temporal region close to the external orbital margin of both eyes in succession, the holding time being from 1 to 5 minutes for each of the areas. Thereupon the device is displaced into the auriculo-temporal area 4 at the level of a projection of the optic decussation and the permanent magnet put in said area first on one side of the head, then on the other side, the application time of the rotating magnetic field being 1 to 5 minutes. Then exposed to the effect of the rotating magnetic field in a similar way are the areas of projection of the visual analyzers on the occipital protuberances 5 (FIG. 3) by putting the main permanent magnet of the device on said areas in succession, the exposure time ranging from 1 to 5 minutes. The treatment session terminates in applying the effect of the rotating magnetic field to the region 1 of the bridge of the nose (FIGS. 1, 2) by placing thereon the main permanent magnet of the device, the exposure time being within 1 and 5 minutes. It should be noticed that the exposure time for each of said areas is individual for every patient.

It is worth noting that individual selection of the exposure time of a rotating magnetic field in each of the areas to be treated is determined by the onset of some disagreeable sensations, such as headache and a sense of pressure in the area of the eyeball. The exposure time is to be so varied that such untowards side effects have no time enough to occur.

A rotating magnetic field is featured by such parameters as the induction value and the field intensity vector, i.e., the direction of a magnetic field.

Rotation of a magnetic field results in that the magnetic field induction value at a given point in space or on the area being treated, passes twice through the whole range of magnitudes from the maximum to the minimum per its complete revolution, with the axis of rotation of the main permanent magnet or magnets building up the magnetic field, remaining stationary. The field intensity vector, i.e., the direction of a line of force of the magnetic field, performs also a complete revolution per field revolution. Thus, both the induction value and the direction of the magnetic field vary in the area of the field application during rotation of the main permanent magnet.

As is known from electrodynamics, variation of a magnetic flux (i.e., magnetic field induction) with time induces an electric field in the area when said variation takes place, said electric field enveloping the variable magnetic flux. In this case the value of intensity of the thus-induced electric field depends on the rate of variation of the magnetic flux, i.e., it depends on the maximum and minimum values of the magnetic field induction in the area involved and on the time of said magnetic flux variation. This means that the higher the maximum induction value and the shorter the time of its variation down to the minimum value, or vice versa, the higher the value of intensity of the electric field induced. When interacting with ions in the vessels, axons, neurons, and other cells or in the intercellular space, an induced electric field results in arising of induced currents, i.e., in transfer of ions along the electric field lines of force, the rate of ion transfer being in direct proportion with the electric field intensity. It is common knowledge that such currents provide for a therapeutic action due to their effect on cell metabolism. Besides, the magnetic field itself is capable of producing a therapeutic effect, thus enlarging vascular lumen, reducing blood coagulability, enhancing tissue oxigenation, abating inflammatory processes, accelerating resolution of hematomas, and so on.

The results of the work done, clinical experiments and estimations demonstrate that a maximum magnetic field induction below 0.1 T fails to provide a stable therapeutic effect, nor can it give an adequate treatment efficacy and cut down the treatment time.

A maximum magnetic field induction in excess of 0.25 T, whenever the exposure time in the aforesaid areas is to be cut down, is not practicable since it involves more side effects.

Besides, it is due to sluggishness of setting a new level of dynamic metabolic equilibrium in the course of magnetic field application that a reduced exposure time restricts a possibility of attaining a positive therapeutic effect. Thus, application of magnetic fields having their induction above 0.25 T is undesirable.

It is due to sluggishness of setting a new level of dynamic metabolic equilibrium in the aforesaid areas in the course of their exposure to the effect of a rotating magnetic field that the exposure time of said areas shorter than 1 minute is inefficient and prolongs the treatment course, whereas the exposure time longer than 5 minutes results in the onset of untoward side effects, such as headache, abnormally high intraocular pressure, conjunctivitis, and so on, since permanent and variable magnetic fields, as well as an electric field induced by the latter magnetic field and the respective induced currents must not be applied for a prolonged period of time because of their modifying effect produced on tissue metabolism.

Rotation of a magnetic field at a variable angular velocity and synchronization of its rotation with blood flow pulsation in the internal carotid artery provide for enhanced visual functions, add to the efficacy of treatment of the optic tract and cut down the treatment period.

Figure 5:
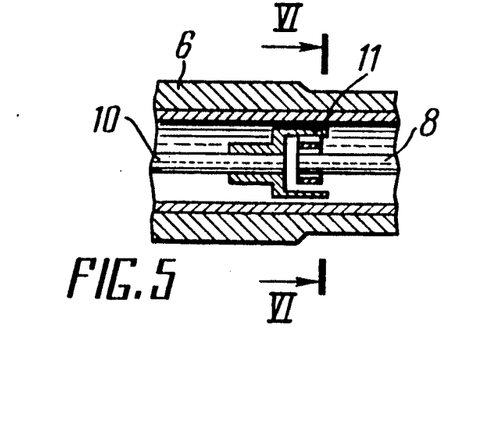
FIG. 5 is a fragmentary sectional view of a device for treatment of diseases of the optic tract, incorporating an elastic element made as a flat spiral spring.
Figure 6:
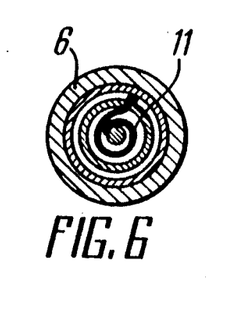
FIG. 6 is a section taken along the line VI—VI in FIG. 5.
Figure 7:
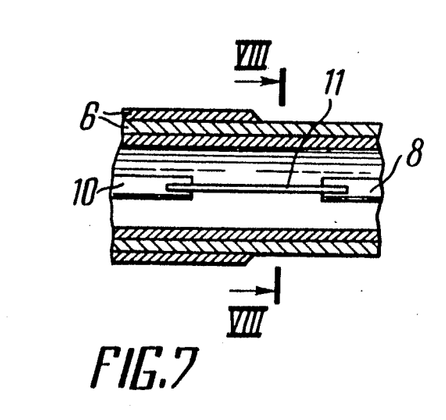
FIG. 7 is a fragmentary sectional view of a device for treatment of diseases of the optic tract, incorporating an elastic element made as a lath spring.
Figure 8:
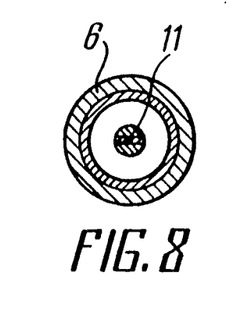
FIG. 8 is a section taken along the line VIII—VIII in FIG. 7.
Figure 9:
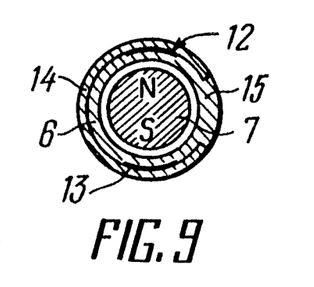
FIG. 9 is a section taken along the line IX—IX in FIG. 4.

The device for carrying the aforesaid method into effect incorporates a housing 6 (FIG. 4), wherein there are accommodated a main permanent magnet 7 having an axle 8, and a drive 9 whose shaft 10 is connected to the axle 8 through an elastic element 11, which may be shaped as a coil spring, flat spiral spring (FIGS. 5, 6) or lath spring (FIGS. 7, 8). The housing 6 (FIG. 4) accommodates also a magnetic brake 12, which is located in the effective area of the magnetic field and is shaped as two ferromagnetic rods 13 (FIG. 9).

Figure 10:
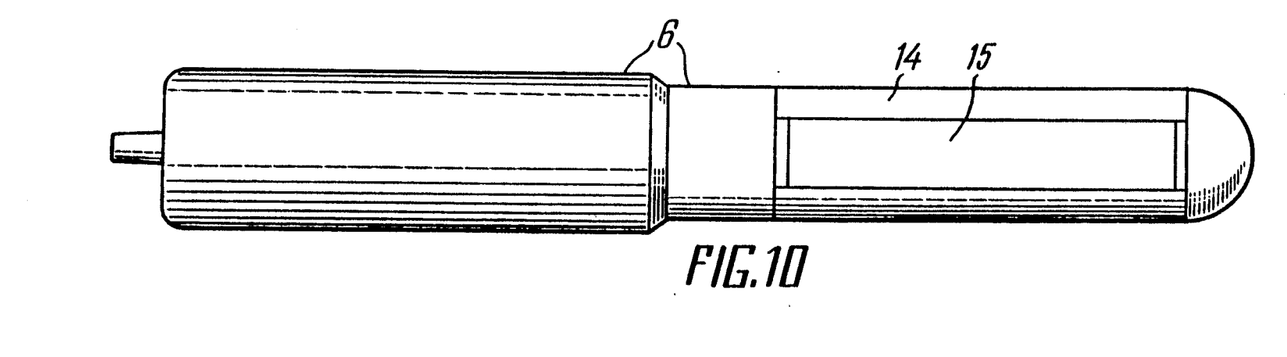
FIG. 10 is a general view of a device for treatment of diseases of the optic tract, according to the invention.

The device for treatment of diseases of the optic tract comprises also a shield 14 (FIG. 10) having a window 15 and arranged round the main permanent magnet 7 (FIG. 4) in the magnetic field effective area, said shield being made of a high-conductance material.

Figure 11:
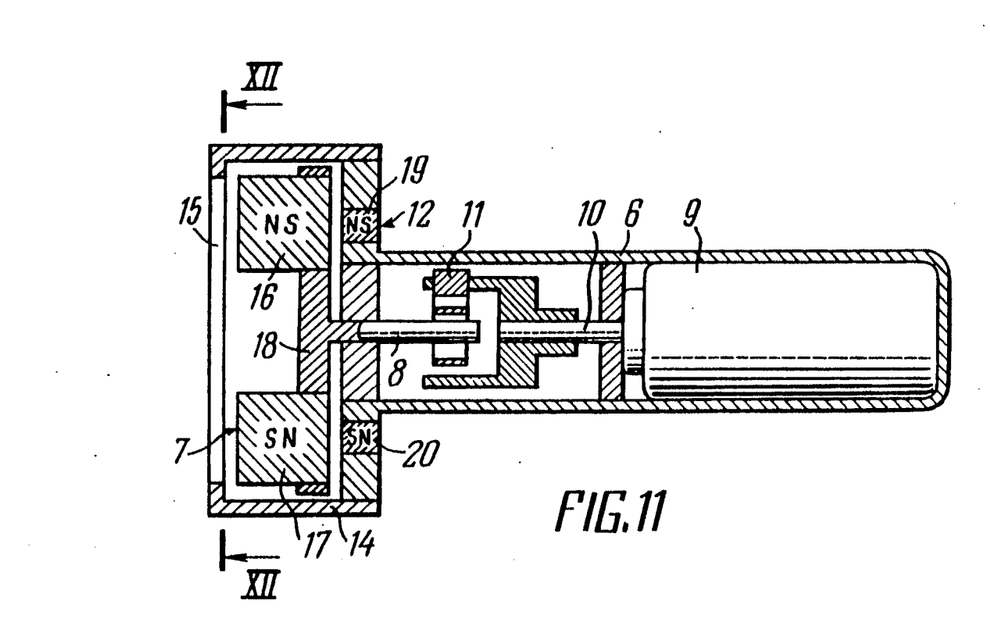
FIG. 11 a general sectional view of an alternative embodiment of the device of FIG. 10, according to the invention.
Figure 12:
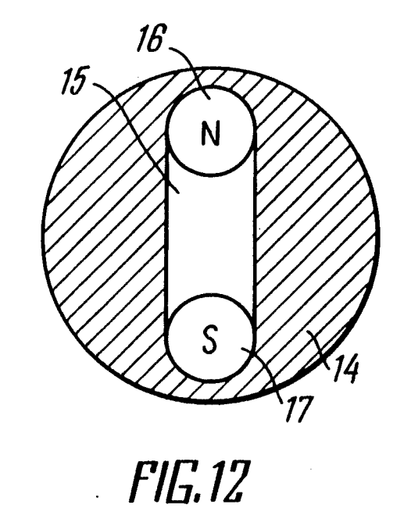
FIG. 12 is a section taken along the line XII—XII in FIG. 11.

Now let us consider an embodiment of the device for treatment of diseases of the optic tract as presented in FIG. 11. The main permanent magnet 7 of the device is composed of two magnets 16 and 17 secured with their opposite poles on a faceplate 18 made of, e.g., a ferromagnetic material. The magnetic brake 12 is built up of two permanent magnets 19, 20 accommodated in the housing 6 under the faceplate 18 so that their poles are oriented oppositely with respect to the faceplate 18. The elastic element 11 is shaped as a flat spiral spring. FIG. 12 illustrates the position of the window 15 of the shield 14.

Figure 4:
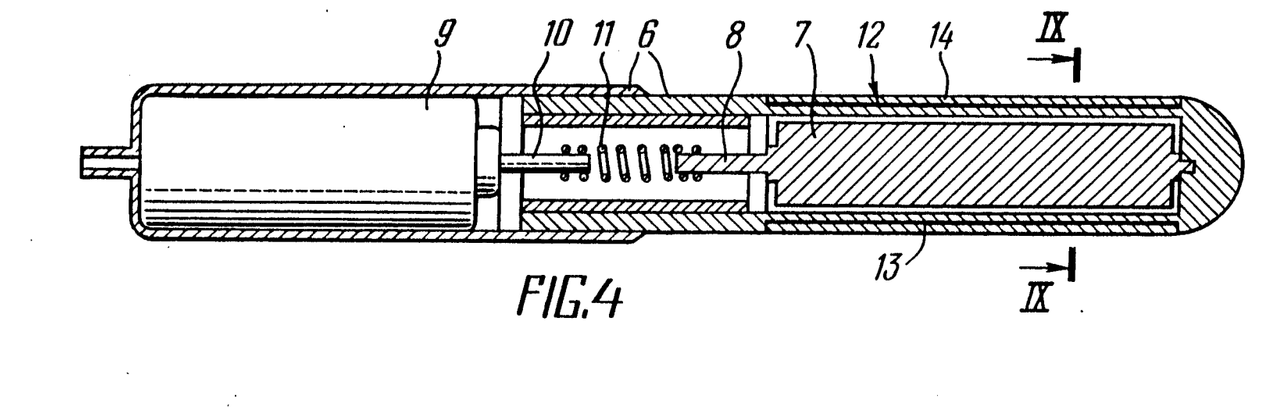
FIG. 4 is a general sectional view of a device for treatment of diseases of the optic tract, according to the invention.

The device for treatment of diseases of the optic tract as shown in FIG. 4 functions as follows.

The ferromagnetic rods 13 of the magnetic brake 12 provide for strict orientation of the poles of the main permanent magnet 7 with respect to the housing 6. Once the shaft 10 of the drive 9 has started rotating the elastic element 11, viz., the spring begins twisting (i.e., to be wound on), this being due to the fact that the ferromagnetic rods 13 of the magnetic brake 12 keep the main permanent magnet 7 fixed stationary, so to say 'enslaved'. The elastic element 11, i.e., the spring is being wound on until the torque on the axle 8 of the main permanent magnet 7 gets equal to the torque developed due to magnetic adherence of the main permanent magnet 7 to the ferromagnetic rods 13. Once the torque of the wound-up spring (the elastic element 11) has become equal to that developed by magnetic adherence of the main permanent magnet 7 to the ferromagnetic rods 13, with the shaft 10 of the drive 9 rotating, there occurs, so to say, 'failure' of the magnetic brake 12, i.e., the main permanent magnet 7 starts rotating.

As soon as the force applied to the axle 8 of the main permanent magnet 7 by the wound-up spring becomes equal to the force of magnetic adherence of the main permanent magnet 7 to the ferromagnetic rods 13 the angular velocity of rotation of the main permanent magnet 7 gets equal to zero. With the shaft 10 of the drive 9 rotating and the spring in the wound-up state the main permanent magnet 7 starts rotating. As the angle of rotation of the main permanent magnet 7 increases the force of magnetic adherence of the latter to the ferromagnetic rods 13 drops due to a longer distance therebetween, with the result that the angular velocity of rotation of the main permanent magnet 7 begins to increase. Once the axle 8 of the main permanent magnet 7 has revolved through 90 degrees the forces of magnetic adherence of the opposite poles of the main permanent magnet 7 to the ferromagnetic rods 13 get equal but oppositely directed, while a total force of magnetic adherence becomes equal to zero. As soon as the axle 8 of the main permanent magnet 7 rotates through an angle greater than 90 degrees, the force of magnetic adherence of its poles to the ferromagnetic rods 13 becomes an analogue of a couple of forces, since its direction coincides with the sense of rotation of the magnet 7.

Once the angular velocities of the shaft 10 of the drive 9 and of the axle 8 of the main permanent magnet 7 have equalized, the forces of magnetic adherence of the poles of the main permanent magnet 7 to the ferromagnetic rods 13, as well as the force of the unwinding spring get equal, while the angular velocity of the axle 8 of the main permanent magnet 7 starts rising rapidly. At the instant when the angle of rotation becomes equal to 180 degrees the force of magnetic adherence of the poles of the main permanent magnet 7 reaches its maximum value and acceleration of magnetic field rotation becomes also maximum. As a result, the angular velocity of rotation of the axle 8 of the main permanent magnet 7 and hence that of the magnetic field get maximum. In this case the angular velocity of rotation of the shaft 10 of the drive 9 proves to be below the angular velocity of rotation of the axle 8 of the main permanent magnet 7, while the degree of winding-on of the spring decreases.

Once the axle 8 of the main permanent magnet 7 has revolved through an angle exceeding 180 degrees, its angular velocity of rotation starts decreasing. This is explained by the fact that the force of magnetic adherence of the poles of the main permanent magnet 7 to the ferromagnetic rods 13 has reached its maximum value, the spring is unwound completely, the angular velocity of rotation of the shaft 10 of the drive 9 is below that of the axle 8 of the main permanent magnet 7 so that the kinetic energy of rotation stored by the main permanent magnet 7 is the only principal factor of rotation. As soon the interaction of the poles of the main permanent magnet 7 dampens out its rotary inertia, the angular velocity goes to zero, whereas the force of magnetic adherence of the main permanent magnet 7 urges it to reverse the sense of its rotation. As a result, a few rotary oscillations of the main permanent magnet 7 occur about a point corresponding to an angle of 180 degrees, which oscillations will continue until unidirectional rotation of the shaft 10 of the drive 9 makes the spring to wind up so as its force of tension becomes equal to the forces of magnetic adherence of the polses of the main permanent magnet 7 to the ferromagnetic rods 13, whereupon the whole process of rotation of the permanent magnet 7 will be repeated.

In an embodiment of the device as shown in FIG. 11 used as the magnetic brake 12 are the permanent magnets 19 and 20, which are arranged diametrically opposite with respect to the axle 8 of rotation of the main permanent magnet 7 and are oriented with their opposite poles relative to the faceplate 18, the latter being made of, e.g., a ferromagnetic material.

Since magnetic adherence takes place of the permanent magnets 19 and 20 to the faceplate 18 similar to that described above, characteristic features of rotation of the main permanent magnet 7 (15, 16) on the faceplate 18 are similar to those described with reference to the embodiment considered hereinbefore.

Characteristic features of the permanent magnet rotation are somewhat modified in the case where the faceplate 18 is made of a nonferromagnetic material.

In this case use of the magnets 19, 20 oriented with their like poles relative to the faceplate 18 fails to provide the desired effect of increased angular velocity of the main permanent magnet 7, which precludes the full accomplishment of the objects of the invention. This is accounted for by the fact that at any angle of rotation of the main permanent magnet 7, its interaction with the permanent magnets 19, 20 develops forces that are equal in magnitude but directed oppositely. In addition, the relative position of the main permanent magnet 7 and the housing 6 is not fixed.

Whenever the permanent magnets 19 and 20 are oriented with their unlike poles with respect to the faceplate 18, there occurs a well-defined position of the main permanent magnet 7 with respect to the housing 6. However, having once rotated through 90 degrees the main permanent magnet 7 (16, 17) starts interacting with the permanent magnets 19, 20 by virtue of mutual repulsion, i.e., deceleration of rotation of the main permanent magnet 7 (16, 17).

This results in that the angular velocity of rotation of the main permanent magnet 7 (16, 17) passes through its minimum with an angle of rotation equal to 180 degrees. Further velocity rising process occurs similarly to the embodiment of the device shown in FIG. 4. Thus, in the herein-considered embodiment of the device the angular velocity of rotation of the main permanent magnet 7 (16, 17) passes through its maxima at an angle of 90 degrees and through its minimum at an angle of 180 degrees during rotation of the main permanent magnet 7 (16, 17) through an angle of 180 degrees, whereupon said angular velocity starts increasing, which has been the case with the embodiment of the device presented in FIG. 4.

In an embodiment of the device making use of either of the permanent magnets 19 or 20 oriented with either of its poles with respect to the faceplate 18, a well-defined fixing of the main permanent magnet 7 (16, 17) with respect to the housing 6 is attained, as well as the same mechanism and characteristic features of its rotation as in the case of the ferromagnetic faceplate 18.

Thus, a variable angular velocity of rotation of the main permanent magnet 7 (16, 17) may be attained, in the case of high acceleration values, in all cases save an embodiment involving similar orientation of the poles of the permanent magnets 19, 20 with respect to the faceplate 18 made of a nonferromagnetic material.

The device for treatment of dieseases of the optic tract is so positioned in each of the areas 1 through 5 to be treated (FIGS. 1 through 3) that the main permanent magnet 7 (16, 17) would rotate over said area at an angular velocity varying within a maximum possible range. In this case, with a view to reducing the magnetic field leakage flux the window 15 (FIGS. 10, 12) of the shield 14 is located over the area to be exposed to the effect of the magnetic field.

Thus, the embodiments of the device described above provide for magnetic field rotation at a variable angular velocity and hence its change as for amplitude and direction, which affords, in combination with the method disclosed herein, enhancing of the visual functions, higher efficacy of treatment and curtailed treatment period.

The proposed method for treatment of diseases of the optic tract and the device for carrying said method into effect are illustrated hereinbelow by the following exemplary clinical case histories.

EXAMPLE 1

Female patient who had sustained myelopolyradiculoneuritis, noticed affected visual acuity in both eyes. Retrobulbar neuritis was diagnosed. After conservative treatment visual acuity in OD remained equal to 0.5, in OS, 0.3 to 0.4. Fields of colour vision narrowed by 20 degrees. According to automatic perimetry findings, reduced light sensitivity in OD (relative narrowing of the visual field to 30 degrees from the fixation point), narrowed visual field in OS on the nasal side, multiple relative scotomata in the inferonasal portions of the visual field. According to the evidence of electrophysiological examinations, moderate changes in the inner layer of the retina and in the optic nerve.

On examination of the fundus oculi—the optic disk pallid on the temporal side, the arteries narrowed and tortuous. No changes in the macular zone. The patient was given 15 one-minute sessions of magnetic stimulation with a magnetic field having an induction of 0.1 T. As a result, visual acuity in OD increased to 0.6, that is OS, to 0.6. Fields of colour vision extended by 10 degrees. According to the evidence of automatic perimetry relative scotomata disappeared from the visual field, the peripheral borders extended by 10 degrees. According to the findings of electrophysiological examination the inner layers of the retina in a normal state, slight changes in the optic nerve. The follow-up period—10 months.

EXAMPLE 2

Female patient noted visual impairment from June 1986. Maculodystrophy in OD was diagnosed. Visual acuity in OD $0.3+1.0d-0.5$. Electrical sensitivity 'threshold' equal to 100 $\mu$A gave evidence of moderate changes in the inner layers of the retina. The evidence available testified to exudative dysfunction of the pigmented epithelium and of the photoreceptors. The visual field narrowed concentrically by 30 degrees. According to the findings of automatic perimetry there were noted multiple paracentral scotomata and narrowed peripheral borders by 30 degrees.

The patient was examined by a neuropathologist in order to detect the cause of retinal dystrophy. The examination findings: vegetovascular dystonia against a background of osteochondrosis, angiospasm of the cerebral vessels accompanied by hypertensive disease and metabolic polyarthritis in the course of involution.

Ocular fundus evidence—the optic disk coloured light pinkish, its borders clear-cut, the arteries narrowed and tortuous. Some dystrophic changes in the retina (of the cystose type) at the periphery and in the central zone. The patient was subjected to 15 two-minute sessions of magnetic stimulation with a magnetic field having an induction of 0.1 T. The patient tolerated the treatment course well. Headache that had troubled the patient earlier disappeared in the course of treatment. Visual acuity in OD increased to 0.8. According to the evidence of automatic perimetry the borders of the visual field normalized. The electrical sensitivity 'threshold' dropped down to 70 $\mu$A, which evidenced slight changes in the inner layers of the retina.

EXAMPLE 3

Male patient had detected drastic visual impairment in OD a year before resorting to a clinic. Visual impairment resulted from circulatory disturbance in the vessels suppling the optic nerve. No improvement in the patient's sight ensured from conservative treatment performed. Visual acuity 0.02 (ex) in OD, $0.2+1.0d=0.6$ in OS. The visual field in OS narrowed concentrically to 10 degrees, no visual field in OD on the nasal side, while on the temporal side it narrowed to 30°. According to the findings of electrophysiological examinations bad changes in the inner layers of the retina and in the optic nerve.

According to the evidence of computerized tomography the diameter of the right and left optic nerve 4.3 mm, density of the right nerve 21.3 N units, that of the left nerve, 47 N units.

Ocular fundus in OD—the optic disk pallid, its borders clear-cut, the arteries narrowed and tortuous.

Ocular fundus in OS—the optic nerve disk coloured white, its borders clear-cut, slight parapapillar edema. The arteries narrowed and tortuous, the veins moderately dilated.

The patient underwent 15 5-minute sessions of magnetic stimulation with a magnetic field having an induction of 0.1 T. After the treatment the visual acuity in OD increased to $0.3+2.0d=0.8$, that in OS, to $0.4+2.0d=1.0$.

The borders of the visual fields extended by 25 degrees. According to the evidence of electrophysiological examinations, moderate changes in the inner layers of the retina and in the optic nerve. The follow-up period—one year. Visual acuity remains unaffected, the borders of the visual field has narrowed by 5 degrees.

EXAMPLE 4

Male patient had noticed drastic visual impairment in OS six month before resorting to the clinic. Ischemic neuroretinopathy was diagnosed. The patient was treated conservatively without any positive effect.

Visual acuity in OS, 0.01, unamenable to correction, that of OD $0.3+2.5d=0.4$.

The visual field of the OS narrowed concentrically to 35 degrees, that of OD remained unaffected.

Electrophysiological examinations detected considerably changes in the inner layers of the retina and in the optic nerve of OS and moderate changes in the inner layers of the retina and in the optic nerve of OD.

Occular fundus: OS—the optic disk edematous, its borders blurred and undeterminable, polymorphic hemorrhages along the run of the inferior vascular bundle and the anteromacular artery, the macular region unaffected; OD—the optic disk light pinkish, its borders clear-cut, sporadic dystrophic foci in the macular zone.

The patient was given 15 one-minute sessions of magnetic stimulation with a magnetic field having an induction of 0.2 T in each area. After treatment the visual acuity in OS increased to $0.1+3.0d==0.6$, that of OD, to 0.6. The visual field of OS extended by 20 degrees.

Electrophysiological examinations demonstrated an improved state of the inner layers of the retina and of the optic nerve; the electrical sensitivity 'threshold' in OD 40, that in OS, 90; electrical lability in OD 40, in OS, 38.

The ocular fundus of OS exhibited lower amount of hemorrhages, no recent hemorrhages were noted.

The follow-up period—6 months, the results of treatment stable.

EXAMPLE 5

Male patient had noticed drastic visual impairment in OD 1.5 years before resorting to medical aid. Visual acuity in OS dropped gradually for 1.5 years. The patient's anamnesis included diabetes mellitus.

On applying to an ophthalmologist there were diagnosed circulatory disturbance in the vessels supplying the right optic nerve, as well as angiosclerosis and maculodystrophy in OS.

Visual acuity in OD 0.01, unamenable to correction, that of in OS, $0.1 + 1.5d$ cyl $- 1.5d = 0.2$. The visual field in OD absent on the temporal side, a relative central scotoma revealed in the visual field of OS, as well as concentric narrowing of the borders on the nasal side by 10 degrees. The field of colour vision narrowed by 20 degrees in OS, while the visual field for red and blue colours in OD narrowed by 20 degrees; no visual field for green colour whatever.

According to the findings of electrophysiological examinations neither the electrical sensitivity 'threshold' nor electrical lability was determinable in OD; moderate changes in the retina and optic nerve were detected in OS. Computer tomography revealed some atrophic changes in the optic nerves of both eyes. Angiosclerosis accompanied by calcinosis in the vascular channel of the internal carotid arteries and of the opthalmic arteries. Age-dependent hydrocephalus. Ultrasonic dopplerography revealed a reduced blood supply of the brain and eye, and atherosclerosis-based stenotic processes.

The patient was subjected to 10 2-minute sessions of magnetic stimulation with a magnetic field having an induction of 0.2 T, applied to each area to be treated. Posttreatment visual acuity in OD increased to 0.3, that of OS, to 1.0. The visual fields in both eyes extended by 20 degrees, relative scotomata disappeared from the visual field of OD. The borders of the field of colour vision extended by 10 degrees.

The follow-up period—one year. The treatment results stable.

EXAMPLE 6

Male patient sustained a traumatic lesion of his right eye in 1982. Visual acuity reduced to 0.4. The patient was given conservative treatment courses which proved to be futile.

The peripheral borders of the visual field remained unaffected. The visual fields for red and green colours narrowed to 10 degrees, while that for blue colour was absent altogether. Computerized perimetry revealed some reduction of foveal light sensitivity to 34 db. Almost complete loss of the lower half of the visual field, with the central zone remaining relatively unaffected. Electrophysiological examinations detected moderate changes in the functions of the outer layers of the retina; electroretinogram enlarged, an indirect symptom of optic nerve pathology.

Ultrasonic dopplerography revealed blood supply of OD reduced to 1 ml/s. Computerized tomography found nonuniform attenuation of the right optic nerve, at some places down to 2.0 mm, its density dropped down to 20N units. Moderate induration of the internal carotid arteries at the level of the clinoid plate; the left optic nerve of normal thickness and density.

The patient was given 15 5-minute sessions of magnetic stimulation with a magnetic field having an induction of 0.2 T. Visual acuity in OD restored to 0.7.

Computerized perimetry demonstrated that foveal sensitivity remained as low as 32 db, and the lower border of the visual field diminished down to 20°. Dopplerography revealed an improved blood supply of OD. Electroretinogram displayed moderate changes in the central area of the retina.

The follow-up period—6 months. The dynamics remained stable.

EXAMPLE 7

Male patient was given the diagnosis of amblyopia of OD. The visual acuity of the eye had been affected since the age of two years.

Visual acuity in OD—0.3, that in OS—1.0. According to evidence obtained by means of a dioptron, hypermetropia of $+1.0$ was detected in OD. No changes in the visual field were found, nor were any changes detected by electrophysiological examinations.

Computerized perimetry revealed reduced light sensitivity to 28 db, an enlarged blind spot and the presence of relative and absolute scotomata, predominantly on the nasal side.

The patient was given 15 one-minute sessions of magnetic stimulation with a magnetic field having an induction of 0.25 T. Posttreatment visual acuity in OD increased to 1.0. Findings of computerized perimetry and electrophysiological examinations revealed no changes.

The follow-up period—10 months. Visual acuity remained invariably high.

EXAMPLE 8

Male patient had the visual acuity of his right eye affected since childhood.

The patient was sent for advice with the diagnosis of convergent squint, mild-degree hypermetropia, amblyopia.

Visual acuity in OD—$0.03 + 1.5d = 0.05 - 0.1$, that of OS, 1.0. Ocular fundus: OD—manifested destruction of the pigmented epithelium, three small white foci with clear-cut borders over the foveal region.

Electrophysiological examinations found bad dysfunction of the outer layers of the retina. Visual fields free from pathology.

The patient was subjected to 15 2-minute sessions of magnetic stimulation with a magnetic field having an induction of 0.25 T. As a result of the treatment performed visual acuity in OD increased to 0.4. Electrophysiological examinations and examination of the visual field revealed no changes.

The follow-up period—6 months.

High visual acuity persisted.

EXAMPLE 9

Female patient applied to an opthalmologist with the diagnosis of partial atrophy of the optic nerve in both eyes secondary to arachnoiditis sustained a year before.

Visual acuity: OD—0.6; OS—0.5, unamenable to correction.

Electrophysiological examinations detected drastic changes in the inner layers of the retina and in the optic nerve. A complex ultrasonic examination was performed, dopplerography revealed considerable reduction of hemodynamics in the optic nerve of both eyes. The fields of colour vision narrowed to 5 degrees in both eyes, peripheral borders of the visual field narrowed to 20 degrees in OD and to 40 degrees in OS.

Computerized tomography revealed a reduced diameter of both optic nerves to 2.8 mm with substantial changes in their density. Consolidated tissue was revealed in a projection of the right internal carotid artery. The basal cisterns dilated due to moderate cerebral atrophy. The patient was given 15 5-minute sessions of magnetic stimulation with a magnetic field having an induction of 0.25 T applied to each area to be treated.

Posttreatment visual acuity increased to 0.7. The borders of the peripheral visual field extended by 20 degrees, those of the field of colour vision, by 10 degrees.

Ultrasonic dopplerography found an improved blood supply of the optic nerve, though its level remained abnormally low.

The dynamic follow-up observation for a 7-month period demonstrated visual acuity remaining adequately high.

EXAMPLE 10

Female patient was given the diagnosis of partial atrophy of the optic nerve in both eyes. Six months before drastic impairment of visual acuity in OD was noticed, secondary to a hypertensive crisis.

Visual acuity: OD—0.2, OS—0.9.

The ocular fundus exhibited paling of the optic disk on both sides, and angiosclerosis.

Computerized perimetry noted narrowed visual field in the upper portions, largely in OD, relative scotomata in the nasal portion of the visual fields-symptoms of central-genesis dysfunction of the optic nerves. Computerized tomography revealed consolidated tissues, more pronounced in OD, where petrificates were observed.

The patient was subjected to 10 4-minute sessions of magnetic stimulation with a magnetic field having an induction of 0.1 T. As a result, visual acuity in OD increased to 0.4, that in OS, to 1.0. Computerized perimetry revealed considerable positive dynamics. Electrophysiological examinations detected slightly reduced electrical lability (down to 38) in OD.

EXAMPLE 11

Female patient was given the diagnosis of partial atrophy of the left optic nerve secondary to arachnoiditis sustained earlier.

Visual acuity: OD—1.0, OS—0.7 to 0.8.

The ocular fundus displayed paling of the optic disk on the temporal side in both eyes.

Electrophysiological examinations revealed moderate changes in the inner layers of the retina and in the optic nerve. Computerized perimetry found sporadic scotomata along the periphery of the visual field in OD and scotomata in the nasal half of the visual field and along the vertical meridian in OS. Computerized tomograph detected moderate hydrocephalus, multiple sclerosis in the remission stage, partial atrophy of the optic nerve in both eyes.

The patient was subjected to 15 3-minute sessions of magnetic stimulation with a magnetic field having an induction of 0.1 T. Posttreatment visual acuity 1.0 in both eyes. Computerized perimetry detected normalized light sensitivity of the macula lutea, no relative scotoma on the nasal side in OS, whereas an absolute scotoma along the vertical meridian persisted. The data of electrophysiological examinations within norm.

EXAMPLE 12

Female patient was given the diagnosis of partial atrophy of the optic nerves secondary to arachnoiditis sustained ten years before (at the present time the patient is 18 years old).

Visual acuity: OD—0.08, OS—0.1, unamenable to correction.

Ocular fundus in both eyes: the optic disk pallid, borders clear-cut, vascular bed correct.

Fields of colour vision: red—narrowed, blue and green—not discriminated. Computerized perimetry revealed multiple paracentral scotomata in both eyes, largely in the area of projection of the papillomacular bundle.

The patient was subjected to 10 4-minute sessions of magnetic stimulation with a magnetic field having an induction of 0.25 T. Computerized perimetry revealed persisted relative scotomata in the centre and paracentrally in the zone of projection of the papillomacular bundle.

The proposed method for treatment of diseases of the optic tract and the device for carrying said method into effect are contraindicated in the following diseases and under the following conditions:

1. Neoplasms in the area to be exposed to the magnetic effect.
2. Retinal detachment.
3. Purulent iridocyclitis, endophthalmitis, panophthalmitis.
4. Metallic foreign bodies in the eyeball.
5. High intraocular pressure.
6. Pronounced vascularization of the corneal scar.

Practical application of the proposed method for treatment of diseases of the optic tract and of the device for carrying said method into effect are instrumental in:

1. Enhancing visual functions 2 to 15 times as for visual acuity, depending on etiology of the disease, restoring colour perception when the latter has been absent beforehand, reducing the area of scotomata and increasing the visual angle threefold.
2. Attaining higher efficacy of treatment in late results up to one year whenever no favourable results have been obtained with other treatment methods (laser-assisted, pharmacological, reconstructive vasoplasty, acupuncture, and electropuncture).
3. Cutting the treatment period down to 15 days, i.e., to one course, consisting of 15 magnetic therapy sessions.

What is claimed is:

1. A device for the treatment of diseases of the optic tract comprising:
   a housing means for location adjacent to the eye and having a longitudinal axis;
   at least one main permanent magnet with opposite magnetic poles situated across the longitudinal axis and having an axle which is situated within the housing;
   drive means mounted in the housing and having a shaft;
   means operatively connecting the shaft and the axle for rotating the at least one main permanent magnet with a variable angular speed, while the drive means rotates at a constant angular speed;
   a magnetic brake means fixedly secured within the housing for generating a coupling force with the at least one main permanent magnet to keep the at least one main permanent magnet stationary until a force of rotation applied through the means connecting the shaft and the axle to the at least one main permanent magnet by the drive means exceeds the coupling force of the magnetic brake on the at least one main permanent magnet.

2. The device of claim 1, wherein the magnetic brake comprises at least one ferromagnetic rod.

3. The device of claim 1, wherein the magnetic brake comprises at least one permanent magnet.

4. The device of claim 1, wherein the at least one main permanent magnet comprises a pair of main permanent magnets located on opposed sides of the axle.

5. The device of claim 1, wherein the means connecting the shaft and the axle comprises an elastic means.

6. The device of claim 5, wherein the elastic means comprises spring means.

7. The device of claim 1 comprising:
at least two main permanent magnets having opposite poles; and
a face plate in contact with the opposite poles of the at least two main permanent magnets, said magnetic brake comprising a pair of permanent magnets having opposite poles, wherein the opposite poles of the pair of permanent magnets of the magnetic brake are oriented towards the face plate.

8. The device of claim 7, wherein the face plate is made of a ferromagnetic material.

9. The device of claim 1, further comprising a magnetic shield having a window arranged around the at least one main permanent magnet.

* * * * *